United States Patent
Li

(10) Patent No.: US 8,028,705 B2
(45) Date of Patent: *Oct. 4, 2011

(54) TONGUE RETENTION SYSTEM

(76) Inventor: Kasey K. Li, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/557,760

(22) Filed: Sep. 11, 2009

(65) Prior Publication Data

US 2010/0000551 A1   Jan. 7, 2010

Related U.S. Application Data

(63) Continuation of application No. 11/425,121, filed on Jun. 19, 2006, now Pat. No. 7,607,439.

(51) Int. Cl.
- *A61C 5/14* (2006.01)
- *A61C 3/00* (2006.01)
- *A61F 5/37* (2006.01)
- *A61B 1/32* (2006.01)

(52) U.S. Cl. ............ 128/860; 128/861; 128/846; 433/6; 433/7; 600/240

(58) Field of Classification Search .................. 433/6–7, 433/24, 215, 229; 128/859–862, 848; 600/240
See application file for complete search history.

(56) References Cited

U.S. PATENT DOCUMENTS

| | | | |
|---|---|---|---|
| 4,901,737 A | 2/1990 | Toone | |
| 5,373,859 A | 12/1994 | Forney | |
| 5,915,385 A | 6/1999 | Hakimi | |
| 6,422,243 B1 * | 7/2002 | Daram | 128/859 |
| 6,494,209 B2 | 12/2002 | Kulick | |
| 6,675,804 B1 | 1/2004 | Pivovarov | |
| 6,877,513 B2 * | 4/2005 | Scarberry et al. | 128/848 |
| 6,955,172 B2 | 10/2005 | Nelson et al. | |
| 7,073,505 B2 * | 7/2006 | Nelson et al. | 128/848 |
| 2002/0144685 A1 | 10/2002 | Ivanovich et al. | |
| 2004/0045555 A1 | 3/2004 | Nelson et al. | |
| 2004/0045556 A1 | 3/2004 | Nelson et al. | |
| 2004/0049102 A1 | 3/2004 | Nelson et al. | |
| 2006/0005843 A9 | 1/2006 | Nelson et al. | |
| 2007/0289600 A1 | 12/2007 | Li | |

OTHER PUBLICATIONS

U.S. Appl. No. 11/425,121, filed Jun. 19, 2006 in the name of Li, Non-final Office Action mailed Feb. 21, 2008.
U.S. Appl. No. 11/425,121, filed Jun. 19, 2006 in the name of Li, Final Office Action mailed Nov. 25, 2008.
U.S. Appl. No. 11/425,121, filed Jun. 19, 2006 in the name of Li, Notice of Allowance mailed Jul. 15, 2009.

\* cited by examiner

*Primary Examiner* — Patricia Bianco
*Assistant Examiner* — Ophelia Hawthorne
(74) *Attorney, Agent, or Firm* — Levine Bagade Han LLP

(57) ABSTRACT

A tongue retaining system is disclosed herein generally having, in one variation, a two-part system. A covering can be sized to fit at least partially over or upon a tongue of a patient, where the covering has an engagement mechanism positioned thereon. A retaining device, sized to fit within a mouth of the patient, may be positioned upon the teeth and have a corresponding engagement mechanism positioned thereon for temporarily coupling with the engagement mechanism on the covering. Such a system can be used to maintain or hold a natural position of the tongue within the mouth of the patient to maintain patency of the airway passages.

20 Claims, 6 Drawing Sheets

TONGUE RETENTION SYSTEM

CROSS-REFERENCE TO RELATED APPLICATIONS

This application is a continuation of U.S. patent application Ser. No. 11/425,121 filed on Jun. 19, 2006, the content of which is incorporated herein by reference in its entirety.

FIELD OF THE INVENTION

The present invention relates to a system for maintaining a position of a tongue within a mouth of a patient. More particularly, the present invention relates to methods and apparatus for maintaining a natural position of a patient's tongue to prevent the tongue from obstructing an airway, e.g., for the treatment of sleep apnea.

BACKGROUND OF THE INVENTION

The elimination of snoring and the various degrees of hypopnea and apnea have been attempted because of their various effects on the body. Such conditions typically occur due to pathological disturbances during sleep. One of the reasons of sleep disturbance is due to the tongue relaxing to varying degrees. When fully awake, the tongue has a normal tone and position within the mouth as air passes in and out of the lungs during respiration. As shown in FIG. 1A, a partial cross-sectional view of a patient's P oral cavity is illustrated showing a natural position of the patient's tongue T and the positioning of the soft palate SP. Patency of the airway passage AP between the posterior wall of the pharynx and the base of the tongue B is illustrated to show the normal unobstructed airway when the tongue T is retained in its natural position.

However, during sleep, as the tongue becomes lax it may collapse against the posterior wall of the pharynx not only causing snoring, but also obstructing the passage of air to the lungs. As shown in FIG. 1B, the tongue T is shown in its relaxed and collapsed state illustrating the base of the tongue B pushing against the soft palate SP and also obstructing the airway passage AP.

Conditions such as sleep apnea not only causes drops in the blood oxygenation level, but and may also adversely affect the heart by increasing blood pressure and pulse rate. Many aspects of a person's quality of life, such as a person's physical and emotional health, are affected by obstructive sleep apnea, A number of conventional treatments exist. For example, conventional treatments such as mask and nasal continuous positive airway pressure (CPAP) devices are typically utilized but compliance is poor and may cause discomfort in the user. Other treatments such as tongue retaining devices are typically made of soft plastic and utilize a tongue-shaped cavity to hold and maintain the tongue in a forward position. Such devices physically clamp onto the tongue using a mechanical grip or retain a portion of the tongue by utilizing a suction device. However, these methods may generally fail due to discomfort by having the tongue compressed or the suction may fail, thereby releasing the tongue to collapse against the pharyngeal wall.

Accordingly, there is a need for a system which maintains the patency of a person's airways during sleep and which is comfortable enough and easy to use to facilitate compliance by the user.

BRIEF SUMMARY OF THE INVENTION

A tongue retaining assembly may generally comprise, in one variation, a two-part system with a covering sized to lit at least partially over or upon a tongue of a patient, the covering having a first engagement mechanism positioned thereon, and a retaining device sized to fit within a mouth of the patient, the retaining device having a second engagement mechanism thereon for coupling with the first engagement mechanism such that a position of the tongue is maintained within the mouth of the patient.

The tongue retaining covering may be disposed over at least a portion of the tongue and may be positioned to closely fit at least partially over or upon or around the tongue and over or upon or around at least an anterior portion of the tongue. The covering may be varied or altered by the user to cover a greater or lesser portion of the tongue depending upon the desired fit and comfort so long as the covered portion of the tongue is sufficient for the covering to hold onto or against tongue.

Moreover, the covering may be comprised of various materials and structures to attain the desired grip or adherence to the tongue surface. One variation may include a mesh covering placed at least partially over, upon, or around the tongue or tongue anterior. Such a covering may be made from any number of biocompatible materials, including but not limited to, methylmethacrylate, mersilene, silicone, polytetrafluoroethylene, polyester, polyethylene, polypropylene, etc. which may be weaved into a braided, woven, or mesh structure having a variable or uniform pitch. Additionally, this type of structure may allow for the individual fibers to move and/or rotate relative to one another such that when a distal portion of the covering is engaged with the retaining device, the tension imparted upon the covering in the axial direction may urge the braided or woven structure to restrict and conform more closely against the tongue surface. The covering may alternatively be configured as a uniform covering made, for example, from a rubber or distensible elastomeric material such as polyurethane.

The retaining device may be configured, for instance, as a mouthguard to fit upon the user's teeth. The retaining member may further have a platform or surface having a magnet or metallic portion thereupon which extends at least partially within the user's mouth to magnetically couple to a corresponding magnet or metallic portion positioned on the retaining member to hold a position of the tongue against the teeth. The retaining member may thus provide a stable platform for coupling and maintaining a position of the user's tongue in a natural position such that patency of the airway passage between the pharyngeal wall and the base of the tongue is maintained. In other variations, the retaining assembly device may be positioned upon the upper teeth, lower teeth, or both upper and lower teeth of the user Additionally, aside from utilizing a single or two opposing magnets for coupling the covering and retaining device, multiple magnets or mechanically coupling mechanisms may be utilized. For instance, multiple magnets or coupling mechanisms may be positioned uniformly along a proximal surface of the retaining assembly. The covering may accordingly have multiple complementary magnets positioned therealong over the surface of the covering in corresponding positions such that when each corresponding magnet or coupling mechanism is engaged, a secure attachment which is properly aligned may be ensured.

Aside from magnetic coupling, various other mechanical coupling mechanisms may be utilized to provide for a temporary connection between the two. For example, various mechanical connectors, e.g., locking projections, hook-and-loop connectors, etc., may be utilized for creating mechanical coupling mechanisms.

DETAILED DESCRIPTION OF THE INVENTION

Figure 1A:
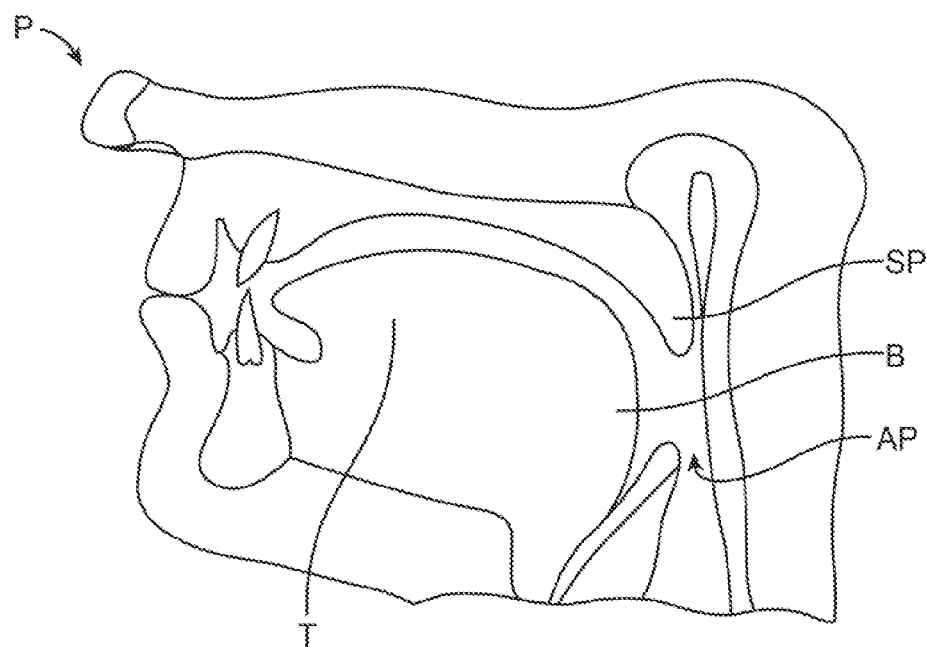
FIG. 1A shows a partial cross-sectional view of a patient's oral cavity illustrating a natural position of the patient's tongue.
Figure 1B:
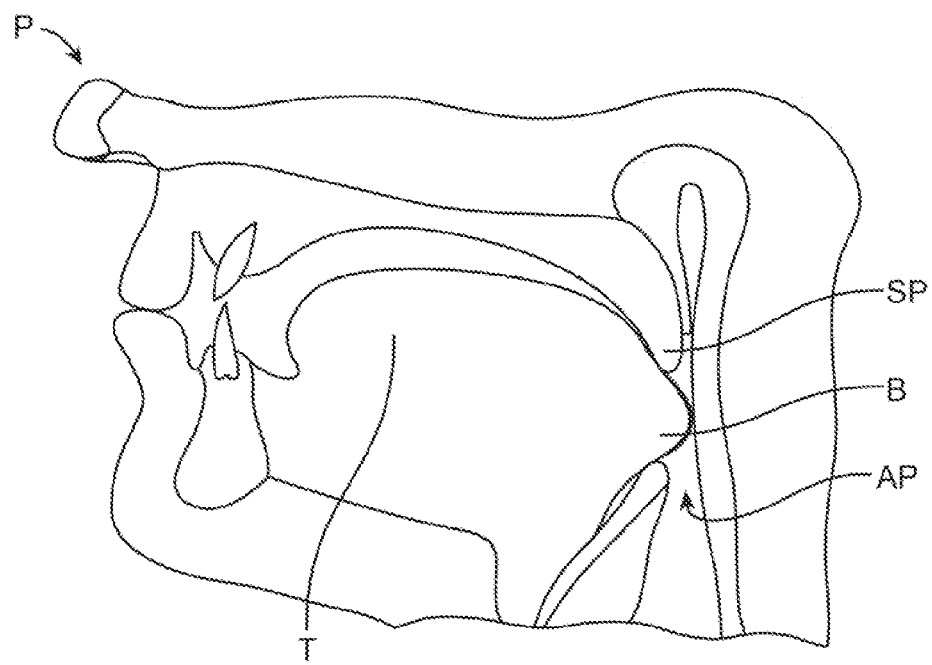
FIG. 1B shows the tongue in its relaxed and collapsed state illustrating the base of the tongue pushing against the soft palate and also obstructing the airway passage.
Figure 2:
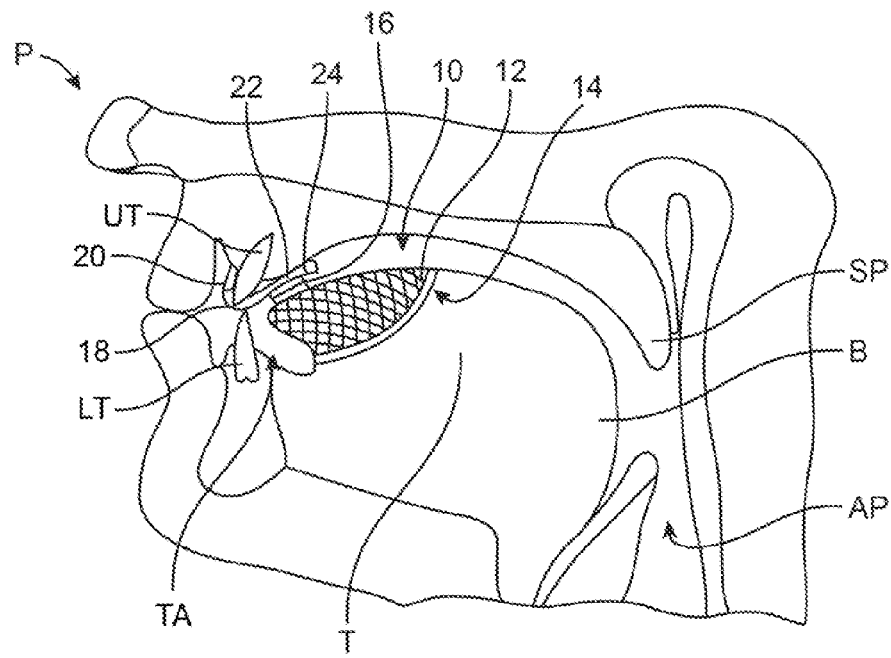
FIG. 2 illustrates one variation of the tongue retaining system for maintaining a position of the tongue by coupling a covering over at least a portion of the tongue with an engagement mechanism positioned on a retaining device retained by the upper teeth.

An example of one variation of the tongue retaining assembly may be seen in the side view of FIG. 2, which shows the oral cavity of a patient P and the soft palate SP. As illustrated, the tongue retaining assembly 10 may generally comprise, in one variation, a two-part system with a tongue retaining covering 12 disposed over at least a portion of the tongue T and a retaining assembly 18 for temporarily coupling with the tongue retaining covering 12. The covering 12 may be positioned to closely fit at least partially over or upon or around the tongue and over or upon or around at least an anterior portion of the tongue TA. Covering 12 may be varied or altered by the user to cover a greater or lesser portion of the tongue T depending upon the desired fit and comfort so long as the covered portion of the tongue T is sufficient for covering 12 to hold onto or against tongue T.

The user may position their tongue through opening 14 and into covering 12 and advanced such that the tongue T fits snuggly within the covering 12 and, in this variation, such that a first magnet 16 located on or near the end of covering 12 is positioned to lie upon or near the tip of tongue T. With the tongue retaining covering 12 desirably positioned upon the tongue T, the retaining assembly 18 may be positioned upon the teeth of the user. In this case, the retaining assembly 18 may be positioned upon the user's upper teeth.

Retaining assembly 18 may be generally comprised of a retaining member 20 configured, for instance, as a mouthguard to fit upon the user's teeth. The retaining member 20 may further have a platform 22 or surface having a second magnet 24 or metallic portion thereupon which extends at least partially within the user's mouth. Once the retaining covering 12 and retaining member 20 have been placed within the user's mouth, the first magnet 16 on covering 12 may magnetically couple to the second magnet 24 or metallic portion on retaining member 20 to hold a position of the tongue T against the teeth. The retaining member 20 may thus provide a stable platform for coupling and maintaining a position of the user's tongue T in a natural position such that patency of the airway passage AP between the pharyngeal wall and the base of the tongue B is maintained.

Alternatively, the user may position the retaining assembly 18 upon the user's teeth prior to placement of covering 12 upon the tongue T. In yet another alternative, the user may simultaneously position the retaining assembly 18 as well as covering 12 within the user's mouth. In either case, having a two-piece retaining assembly allows the user greater flexibility in desirably positioning the individual covering 12 and retaining member 20 to optimize comfort and efficiency.

Figure 3:
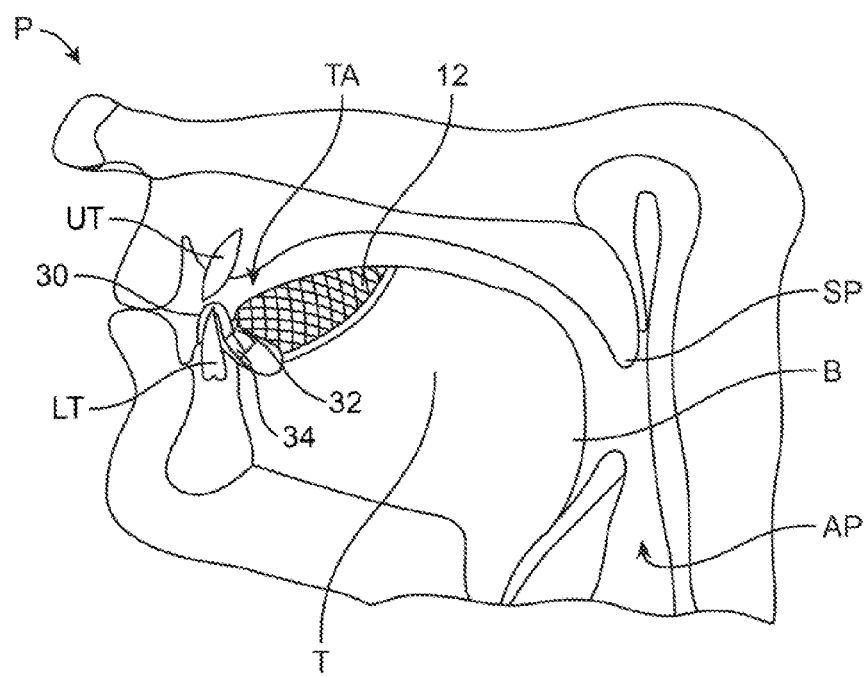
FIG. 3 illustrates another variation of the tongue retaining system maintaining a position of the tongue by coupling a covering over at least a portion of the tongue with an engagement mechanism positioned on a retaining device retained by the lower teeth.

In another variation, rather than having retaining assembly 18 positioned upon the upper teeth UT of the user, a retaining member 30 may be configured for placement upon the user's lower teeth LT, as shown in FIG. 3. In this case, retaining member 30 may likewise have a second magnet 34 or metallic portion positioned upon a proximal surface of the retaining member 30. Covering 12 may also be configured to have a first magnet 32 positioned upon a lower surface of covering 12 to correspondingly couple to retaining member 30 or covering 12 from FIG. 2 may be simply worn upon the tongue T in a rotated manner such that it couples with the retaining member 30 positioned upon the lower teeth LT.

Figure 4:
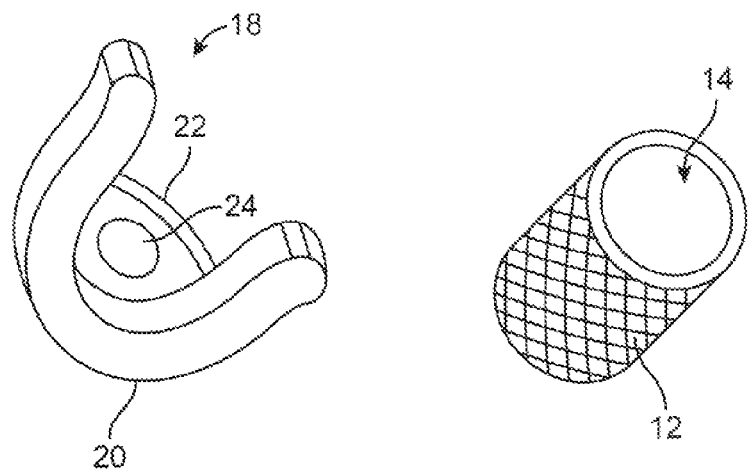
FIG. 4 illustrates a perspective view of a variation of the covering for placement over or upon a portion of the tongue and the retaining device for coupling with the covering.

A perspective view of the tongue retainer assembly 10 is shown in FIG. 4. As seen, retainer assembly 18 may be configured as a mouthguard to fit either upon the upper teeth UT or lower teeth LT of the user. In the variation shown, retaining member 20 may have a platform 22 which extends at least partially into the mouth while having a magnet 24 or metallic portion positioned thereupon. The tongue retaining covering 12 is shown with the opening 14 through which the user may position their tongue.

Figure 5A:
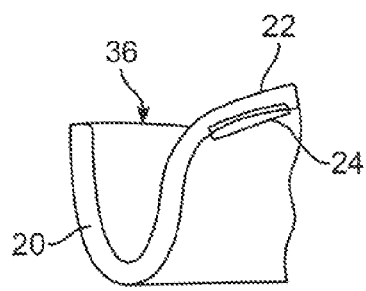
FIG. 5A shows a partial side view of a variation of the retaining device having an engagement mechanism positioned upon a platform extending from the retainer.
Figure 5B:
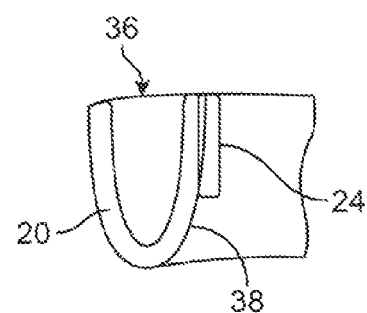
FIG. 5B shows a partial side view of another variation of the retaining device having an engagement mechanism positioned on a proximal surface of the retainer.
Figure 5C:
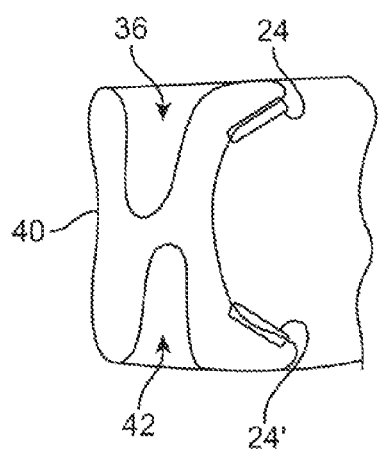
FIG. 5C shows a partial side view of yet another variation of the retaining device having one or more engagement mechanisms positioned on one or more proximal surfaces of the retainer.

FIG. 5A shows a close-up of a partial cross-sectional view of one variation of retaining member 20 illustrating the retaining channel 36 within which the user may position their upper teeth UT to securely hold the member 20. Also shown is the platform 22 which may extend at least partially along the hard palate within the user's mouth and the position of the at least one magnet 24 or metallic portion positioned upon the platform 22. FIG. 5B also illustrates a close-up of a partial cross-sectional view of another variation of retaining member 20 having the at least one magnet 24 or metallic portion positioned directly upon a proximal or posterior retaining surface 38. FIG. 5C shows yet another variation of a combination retaining assembly 40 configured as a mouthguard for receiving both the upper teeth UT within retaining channel 36 and lower teeth LT within retaining channel 42 in a single device. Moreover, one or more magnets 24, 24' may be positioned about the proximal surface of retaining assembly 40 to provide for additional flexibility in coupling the covering 12 to the retaining assembly 40.

Figure 6A:
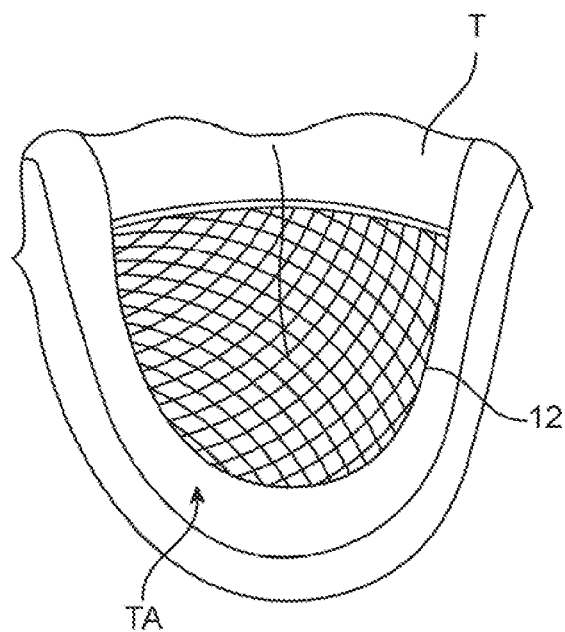
FIG. 6A shows a top view of a variation of the covering made from a mesh material which is adapted to securely retain the tongue when the covering is tensioned in an axial direction.

Aside from the retaining member configuration, covering 12 may be comprised of various materials and structures to attain the desired grip or adherence to the tongue surface. One variation, as shown above, may include a mesh covering 12 placed at least partially over, upon, or around the tongue T or tongue anterior TA, as shown in FIG. 6A. Such a covering 12 may be made from any number of biocompatible materials, including but not limited to, methylmethacrylate, mersilene, silicone, polytetrafluoroethylene, polyester, polyethylene, polypropylene, etc. Fibers, strands, or ribbons of such a material may be weaved into a braided, woven, or mesh structure having a variable or uniform pitch which allows covering 12 to conform closely to the anatomy of the tongue.

Moreover, such a braided, woven, or mesh structure may allow for the individual fibers to move and/or rotate relative to one another such that when a distal portion of covering 12 is engaged with the retaining device, the tension imparted upon the covering 12 in the axial direction may urge the braided or woven structure to restrict and conform more closely against the tongue surface. Thus, as the tongue relaxes and further collapses towards the pharyngeal tissue, the greater the retaining force imparted by covering 12 upon the tongue surface to hold and maintain its position within the patient's mouth. Additionally, covering 12 may be configured and/or adjusted by the user to cover a sufficient portion of the tongue surface so as to distribute the retaining force imparted by covering 12 evenly over the tongue to optimize comfort during use.

Figure 6B:
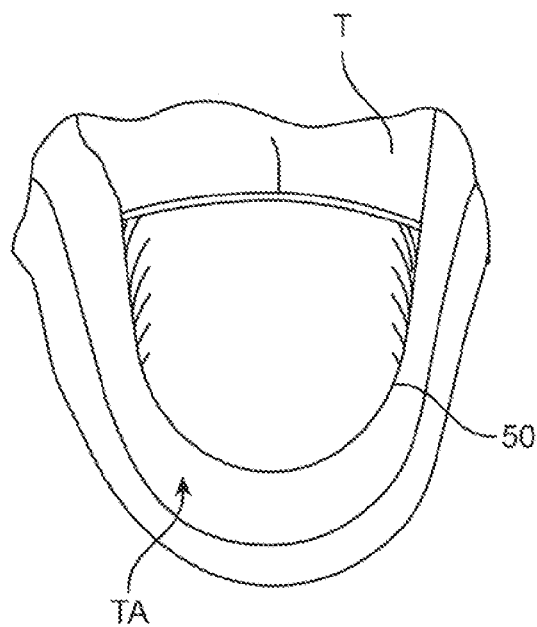
FIG. 6B shows a top view of another variation of the covering made from a distensible material.

Aside from a woven or mesh structure, the covering may alternatively be configured as a uniform covering 50 made, for example, from a rubber or distensible elastomeric material such as polyurethane, as shown in FIG. 6B. In this variation, covering 50 may be simply slipped over a portion of the tongue T and allowed to conform to the tongue anatomy. After use, it may be simply slipped off and removed.

Figure 7:
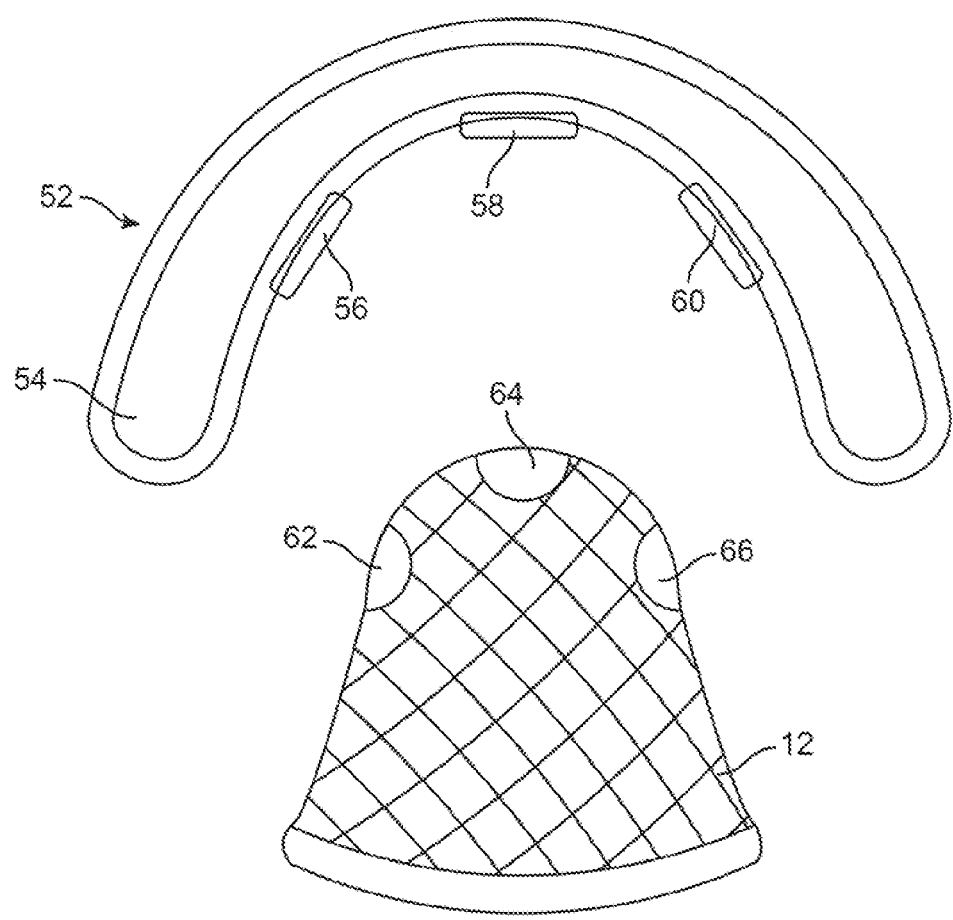
FIG. 7 shows another variation of the tongue retaining system having one or more engagement mechanisms positioned over the retaining device and covering.

Aside from utilizing a single or two opposing magnets for coupling the covering and retaining device, multiple magnets or mechanically coupling mechanisms may be utilized. For instance, FIG. 7 shows an assembly top view of retaining assembly 52 formed as a mouthguard which may be positioned along either the upper or lower row of teeth, or both rows. In this variation, the teeth may be positioned within retaining channel 54 and multiple magnets or coupling mechanisms, in this instance three magnets 56, 58, 60, may be positioned uniformly along a proximal surface of retaining assembly 52. Covering 12 may accordingly have multiple complementary magnets 62, 64, 66 positioned therealong over the surface of covering 12 in positions corresponding to magnets 56, 58, 60 such that when each corresponding magnet or coupling mechanism is engaged, a secure attachment which is properly aligned may be ensured.

Figure 8A:
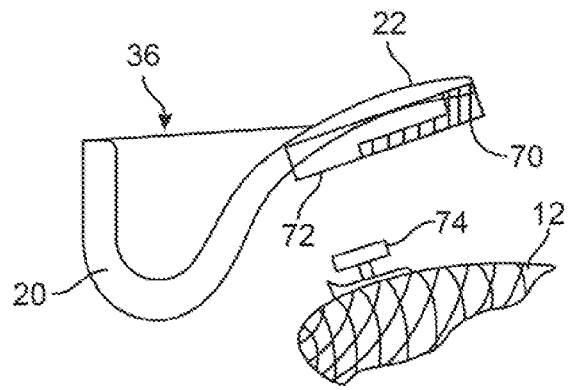
FIGS. 8A and 8B show side and bottom views, respectively, of another variation of a mechanical engagement mechanism between the retaining device and covering.
Figure 8B:
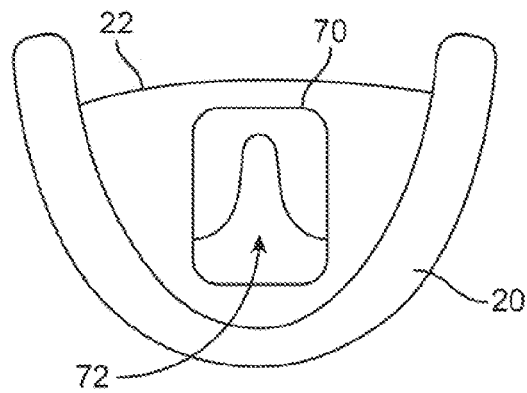
Figure 9:
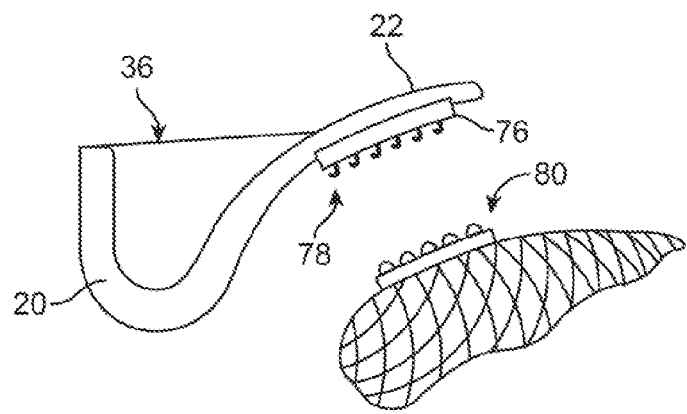
FIG. 9 shows a side view of yet another variation of a mechanical engagement mechanism utilizing hook-and-loop fasteners to temporarily engage the retaining device and covering.

As mentioned above, aside from magnetic coupling between the retaining device and covering, various other mechanical coupling mechanisms may be utilized to provide for a temporary connection between the two. For example, another variation is shown in the side and bottom views of FIGS. 8A and 8B, which show retaining member 20 having a mechanical connector 70 with a curved receiving channel 72 defined therealong. Covering 12 may have a locking projection member 74 positioned thereon which may be slidably received within receiving channel 72 to create a temporary mechanical engagement. To disengage, projection member 74 may be simply slid distally by the tongue to remove projection member 74 from receiving channel 72.

In yet another variation, retaining member 20 and covering 12 may be temporarily coupled together via a hook-and-loop connector, such as VELCRO® (Velcro Industries B.V. LLC, Netherlands). Retaining member 20 may have a hook-and-loop connector 76 mounted thereon having a plurality of hook fasteners 78 while the covering 12 may have a plurality of loop fasteners 80 disposed thereon for connection with connector 76. These variations on connector mechanisms is intended to be illustrative of the various mechanical coupling mechanisms which may be utilized and are not intended to be limiting in any way.

While illustrative examples are described above, it will be apparent to one skilled in the art that various changes and modifications may be made therein. Moreover, various apparatus or procedures described above are also intended to be utilized in combination with one another, as practicable. The appended claims are intended to cover all such changes and modifications that fall within the true spirit and scope of the invention.

What is claimed is:

1. A variable tongue retention apparatus, comprising:
   a covering sized to fit at least partially over or upon a tongue of a patient, wherein the covering is comprised of a material which conforms to an anatomy of the tongue such that the covering imparts upon the tongue a retaining force which increases when the covering is tensioned posteriorly;
   an attachment positioned on an anterior end of the covering such that the attachment is positioned to lie upon or near an anterior portion of the tongue; and
   a retaining member adapted to be secured to the patient in proximity to a mouth of the patient, the retaining device being coupled to the covering via the attachment such that a position of the tongue is at least maintained within the mouth of the patient.

2. The apparatus of claim 1 wherein the retention apparatus comprises an oral appliance sized to fit within the mouth of the patient.

3. The apparatus of claim 2 wherein the oral appliance is adapted to fit upon a lower row of teeth within the mouth of the patient.

4. The apparatus of claim 2 wherein the oral appliance is adapted to fit upon an upper row of teeth within the mouth of the patient.

5. The apparatus of claim 2 wherein the oral appliance is adapted to fit upon both a lower row and an upper row of teeth within the mouth of the patient.

6. The apparatus of claim 1 wherein the covering is comprised of a mesh covering.

7. The apparatus of claim 6 wherein the mesh covering is adapted to securely retain the tongue when the covering is tensioned in an axial direction.

8. The apparatus of claim 1 wherein the attachment comprises a magnetically coupled engagement mechanism.

9. The apparatus of claim 8 wherein the magnetically coupled engagement mechanism comprises a first and a second magnet.

10. The apparatus of claim 1 wherein the covering is sized to fit over at least the anterior portion of the tongue.

11. The apparatus of claim 1 wherein the covering is comprised of a distensible material.

12. The apparatus of claim 1 wherein the attachment comprises a temporary mechanical engagement.

13. A method of retaining a position of a tongue within a mouth of a patient, comprising:

positioning a covering at least partially over or upon a tongue of the patient such that the covering conforms to an anatomy of the tongue, wherein the covering has an attachment positioned on an anterior end of the covering such that the attachment is positioned to lie upon or near an anterior portion of the tongue;

positioning a retaining device in proximity to the mouth of the patient, wherein the retaining device is coupled to the covering via the attachment;

imparting a retaining force upon the tongue via the covering such that a position of the tongue is maintained relative to the mouth; and, increasing the retaining force upon the tongue as the tongue is moved posteriorly such that the covering is conformed more closely against the tongue such that the position of the tongue is maintained.

14. The method of claim 13 wherein positioning a retaining device comprises positioning an oral appliance within the mouth.

15. The method of claim 14 wherein positioning an oral appliance comprises positioning the oral appliance upon a lower row of teeth within the mouth.

16. The method of claim 14 wherein positioning an oral appliance comprises positioning the oral appliance upon an upper row of teeth within the mouth.

17. The method of claim 14 wherein positioning an oral appliance comprises positioning the oral appliance upon a lower row and upper row of teeth within the mouth.

18. The method of claim 13 wherein positioning a covering comprises positioning the covering over at least the anterior portion of the tongue.

19. The method of claim 13 wherein positioning a covering comprises positioning a distensible membrane covering over or upon the tongue.

20. The method of claim 13 wherein positioning a retaining device comprises positioning the retaining device such that the retaining device is contained completely within the mouth of the patient.

* * * * *